(12) United States Patent
Aqad et al.

(10) Patent No.: US 9,671,689 B2
(45) Date of Patent: *Jun. 6, 2017

(54) CHOLATE PHOTOACID GENERATORS AND PHOTORESISTS COMPRISING SAME

(75) Inventors: Emad Aqad, Northborough, MA (US); Mingqi Li, Shrewsbury, MA (US); Joseph Mattia, Framingham, MA (US); Cheng-Bai Xu, Southborough, MA (US)

(73) Assignee: Rohm and Haas Electronic Materials LLC, Marlborough, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/965,339

(22) Filed: Dec. 10, 2010

(65) Prior Publication Data
US 2011/0250537 A1 Oct. 13, 2011

Related U.S. Application Data

(60) Provisional application No. 61/285,516, filed on Dec. 10, 2009.

(51) Int. Cl.
| | | |
|---|---|---|
| *C07J 31/00* | (2006.01) | |
| *G03F 7/004* | (2006.01) | |
| *C07C 381/12* | (2006.01) | |
| *G03F 7/038* | (2006.01) | |

(52) U.S. Cl.
CPC .......... *G03F 7/0045* (2013.01); *C07C 381/12* (2013.01); *C07J 31/006* (2013.01); *G03F 7/0046* (2013.01); *G03F 7/0382* (2013.01)

(58) Field of Classification Search
CPC ..................................................... C07J 31/006
USPC ..................................................... 430/270.1
See application file for complete search history.

(56) References Cited

U.S. PATENT DOCUMENTS

| | | | |
|---|---|---|---|
| 3,743,660 A | 7/1973 | Borrevang et al. | |
| 6,358,665 B1 | 3/2002 | Pawlowski et al. | |
| 7,527,912 B2 | 5/2009 | Ohsawa et al. | |
| 7,569,326 B2 | 8/2009 | Ohsawa et al. | |
| 7,629,108 B2 | 12/2009 | Watanabe et al. | |
| 7,670,751 B2 | 3/2010 | Ohashi et al. | |
| 8,900,794 B2 | 12/2014 | Aqad et al. | |
| 8,956,799 B2 | 2/2015 | Aqad et al. | |
| 9,046,767 B2 | 6/2015 | Aqad et al. | |
| 2007/0122750 A1* | 5/2007 | Yamaguchi et al. | 430/311 |
| 2008/0124656 A1 | 5/2008 | Kobayashi et al. | |
| 2009/0061358 A1 | 3/2009 | Ohashi et al. | |
| 2009/0274978 A1 | 11/2009 | Ohashi et al. | |
| 2010/0062366 A1 | 3/2010 | Nishi et al. | |
| 2010/0062374 A1* | 3/2010 | Nishi et al. | 430/286.1 |
| 2010/0143830 A1 | 6/2010 | Ohashi et al. | |
| 2011/0159429 A1 | 6/2011 | Thackeray et al. | |
| 2012/0129105 A1 | 5/2012 | Thackeray et al. | |
| 2013/0344438 A1 | 12/2013 | Aqad et al. | |

OTHER PUBLICATIONS

Search Report of Counterpart European Application No. EP 10194457 (2 Pages).
Examination Report issued in Counterpart European Applicaiton No. EP 10194457 (2 Pages).
English Language Summary of Office Action issued in Counterpart Japanese Application No. 2010-275276—Dispatch Date: Jan. 23, 2015 (5 Pages).
English Language Summary of Office Action issued in Counterpart China Application No. 201010625251.0.
office Action and Search Report dated Dec. 22, 2015 issued in Chinese counterpart Application 201510090721.0.
English Language Summary of Second Office Action issued in counterpart Chinese Application No. 201510090721.0 (2 Pages), Oct. 31, 2016.
English Language Summary of Second Office Action issued in counterpart Chinese Application No. 201510090721.0 Date of Dispatch: Oct. 31, 2016 (2 Page).

* cited by examiner

*Primary Examiner* — Chanceity Robinson
(74) *Attorney, Agent, or Firm* — Mintz Levin Cohn Ferris Glovsky and Popeo, P.C.; Peter F. Corless

(57) ABSTRACT

New photoacid generator compounds ("PAGs") are provided that comprise a cholate moiety and photoresist compositions that comprise such PAG compounds.

6 Claims, No Drawings

CHOLATE PHOTOACID GENERATORS AND PHOTORESISTS COMPRISING SAME

This application claims the benefit of priority under 35 U.S.C. §119(e) to U.S. application Ser. No. 12/965,339, filed Dec. 10, 2010, the entire contents of which application are incorporated herein by reference.

This invention relates to new photoacid generator compounds ("PAGs") that comprise a cholate moiety and photoresist compositions that comprise such PAG compounds.

Photoresists are photosensitive films for transfer of images to a substrate. They form negative or positive images. After coating a photoresist on a substrate, the coating is exposed through a patterned photomask to a source of activating energy such as ultraviolet light to form a latent image in the photoresist coating. The photomask has areas opaque and transparent to activating radiation that define an image desired to be transferred to the underlying substrate.

Known photoresists can provide features having resolution and size sufficient for many existing commercial applications. However for many other applications, the need exists for new photoresists that can provide highly resolved images of submicron dimension.

Various attempts have been made to alter the make-up of photoresist compositions to improve performance of functional properties. Among other things, a variety of photoactive compounds have been reported for use in photoresist compositions. See, e.g., U.S. Pat. Nos. 6,664,022 and 6,849,374 and U.S. Patent Publication 2009/0061358.

In one aspect, we now provide novel photoacid generator compounds (PAGs) that comprise a cholate moiety for use in either positive-acting or negative-acting photoresist compositions. Preferably the PAG is an ionic compound, particularly a sulfonium compound. In the case of such sulfonium compounds, preferably the cholate group is a moiety of the anionic component of the PAG. For example, in a preferred aspect, the cholate group is a moiety of a fluorinated sulfonate anion compound, particularly where the anion compound comprises an extended saturated linker group as discussed below.

As referred to herein, the term "cholate" is inclusive of steroid structures in general, including $C_{20\text{-}50}$ hydrocarbon groups having a steroid structure. Steroid structures are well-known and suitably may contain three six-membered rings and one five-membered ring fused together as represented by the general formula:

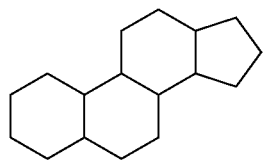

Particularly preferred PAGs of the invention may comprise those of the following Formulae (I) and (II):

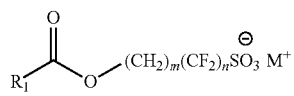

(I)

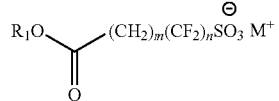

(II)

wherein in each of Formulae (I) and (II):

$M^+$ represent an organic onium salt, in particular aspects $M^+$ is a trisubstituted sulfonium cation or disubstituted iodonium cation.

$R_1$ is a steroid structure;

m is an integer of 0 to 10 and preferably is a positive integer such as at least 1, 2, 3 or 4;

n is a positive integer suitably 1, 2, 3 or 4, more typically 1 or 2. $M^+$ is preferably photoactive.

As discussed above, in a preferred embodiment, PAGs of the invention comprise a sulfonate anion component where a chain that has at least four saturated non-cyclic atoms in interposed between (i) a sulfonic moiety ($SO_3^-$) and (ii) (a) a non-saturated moiety (e.g. phenyl or other carbocyclic aryl), keto (carbonyl), ester and the like or (b) an alicyclic group such as cyclohexyl, and the like. Exemplary anion components may include those of the following formula: $R(CH_2)n(CF_2)_mSO_3-$ where the sum of n and m is at least four, and R is other than a saturated, non-cyclic group (e.g. R may be ester, phenyl, cyclohexyl, etc.).

We have found that such a saturated chain can provide notably enhanced solubility of the PAG compound in typical photoresist solvents such as ethyl lactate, propylene glycol methyl ether acetate and the like.

Preferably, PAGs of the invention are used in positive-acting or negative-acting chemically amplified photoresists, i.e. negative-acting resist compositions which undergo a photoacid-promoted crosslinking reaction to render exposed regions of a coating layer of the resist less developer soluble than unexposed regions, and positive-acting resist compositions which undergo a photoacid-promoted deprotection reaction of acid labile groups of one or more composition components to render exposed regions of a coating layer of the resist more soluble in an aqueous developer than unexposed regions. Ester groups that contain a tertiary non-cyclic alkyl carbon or a tertiary alicyclic carbon covalently linked to the carboxyl oxygen of the ester are generally preferred photoacid-labile groups of resins employed in photoresists of the invention. Acetal groups also are suitable photoacid-labile groups.

Preferred imaging wavelengths of photoresists of the invention include sub-300 nm wavelengths e.g. 248 nm, and sub-200 nm wavelengths e.g. 193 nm and EUV.

Particularly preferred photoresists of the invention contain an imaging-effective amount of one or more PAGs as disclosed herein and a resin that is selected from the group of:

1) a phenolic resin that contains acid-labile groups that can provide a chemically amplified positive resist particularly suitable for imaging at 248 nm. Particularly preferred resins of this class include: i) polymers that contain polymerized units of a vinyl phenol and an alkyl acrylate, where the polymerized alkyl acrylate units can undergo a deblocking reaction in the presence of photoacid. Exemplary alkyl acrylates that can undergo a photoacid-induced deblocking reaction include e.g. t-butyl acrylate, t-butyl methacrylate, methyladamantyl acrylate, methyl adamantyl methacrylate, and other non-cyclic alkyl and alicyclic acrylates that can undergo a photoacid-induced reaction, such as polymers in U.S. Pat. Nos. 6,042,997 and 5,492,793, incorporated herein by reference; ii) polymers that contain polymerized units of a vinyl phenol, an optionally substituted vinyl phenyl (e.g. styrene) that does not contain a hydroxy or carboxy ring substituent, and an alkyl acrylate such as those deblocking groups described with polymers i) above, such as polymers described in U.S. Pat. No. 6,042,997, incorporated herein by reference; and iii) polymers that contain repeat units that comprise an acetal or ketal moiety that will react with photoacid, and optionally aromatic repeat units such as phenyl or phenolic groups.

2) a resin that is substantially or completely free of phenyl or other aromatic groups that can provide a chemically amplified positive resist particularly suitable for imaging at sub-200 nm wavelengths such as 193 nm. Particularly preferred resins of this class include: i) polymers that contain polymerized units of a non-aromatic cyclic olefin (endocyclic double bond) such as an optionally substituted norbornene, such as polymers described in U.S. Pat. No. 5,843,624 incorporated herein by reference; ii) polymers that contain alkyl acrylate units such as e.g. t-butyl acrylate, t-butyl methacrylate, methyladamantyl acrylate, methyl adamantyl methacrylate, and other non-cyclic alkyl and alicyclic acrylates; such polymers have been described in U.S. Pat. No. 6,057,083.

Resists of the invention also may comprise a mixture of distinct PAGs, typically a mixture of 2 or 3 different PAGs, more typically a mixture that consists of a total of 2 distinct PAGs.

The invention also provide methods for forming relief images of the photoresists of the invention, including methods for forming highly resolved patterned photoresist images (e.g. a patterned line having essentially vertical sidewalls) of sub-quarter micron dimensions or less, such as sub-0.2 or sub-0.1 micron dimensions.

The invention further provides articles of manufacture comprising substrates such as a microelectronic wafer or a flat panel display substrate having coated thereon the photoresists and relief images of the invention. Other aspects of the invention are disclosed infra.

In addition to compounds of Formulae I and II above, preferred PAGs of the invention include those of the following Formula (III):

$$(R)-X-(C=O)O(CH_2)_m(CWY)_nSO_3M^+ \quad (III)$$

wherein R is a steroid structure,

X is a linker such as a chemical bond, $C_{1-10}$ carbon or hetero (e.g. N, O or S) chain and the like;

W and Y are each independently in each occurrence hydrogen or fluoro, but where the carbon group directly adjacent to the $SO_3^-$ preferably has at least one fluoro atom and more preferably has at least two fluoro atoms (i.e. $-CF_2-$);

m, n and M+ are the same as defined for Formulae (I) and (II) above.

Yet additional preferred PAGs of the invention include those of the following Formula (IV):

$$(R)-X-O(C=O)(CH_2)_m(CWY)_nSO_3M^+ \quad (IV)$$

wherein R is a steroid structure,

X is a linker such as a chemical bond, $C_{1-10}$ carbon or hetero (e.g. N, O or S) chain and the like;

W and Y are each independently in each occurrence hydrogen or fluoro, but where the carbon group directly adjacent to the $SO_3^-$ preferably has at least one fluoro atom and more preferably has at least two fluoro atoms (i.e. $-CF_2-$);

m, n and M+ are the same as defined for Formulae (I) and (II) above.

Generally PAGs of the invention include the following (in the below structures M+ is the same as defined above for Formulae (I) and (II), and the groups R, m and n are defined directly below the specified compound):

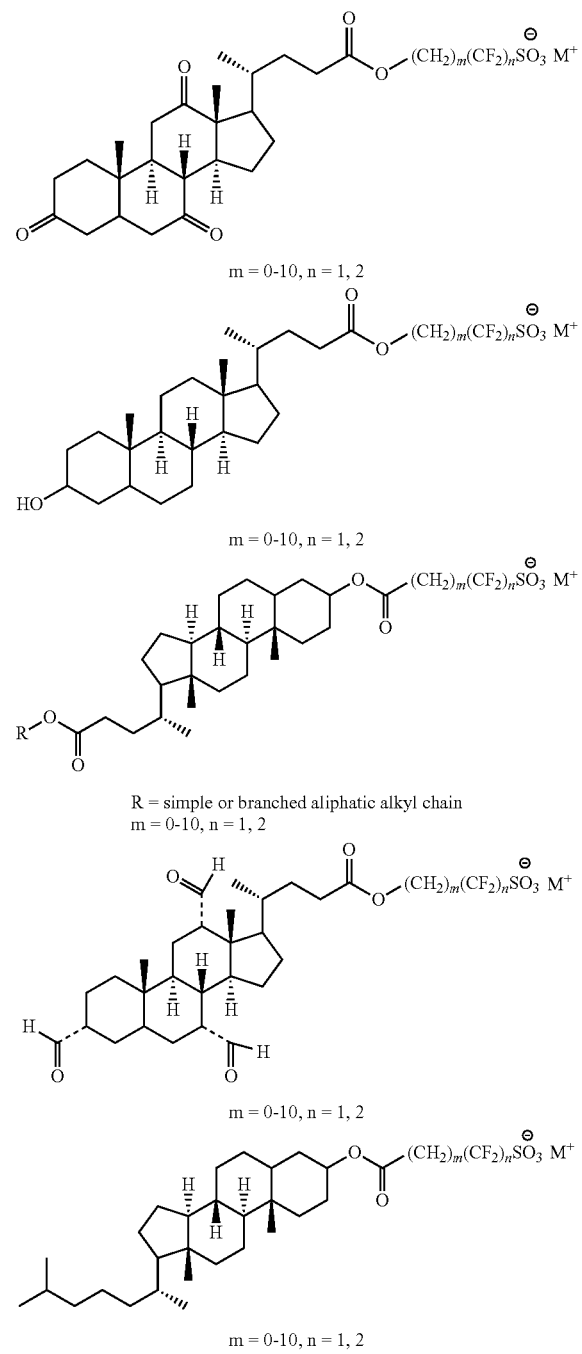

Generally preferred onium salts of PAGs of the invention (including groups $M^+$ in the above formulae) include sulfonium and iodonium salt photoacid generators, such as those compounds disclosed in published European application 0 708 368 A1. Such salts include those represented by the following formula:

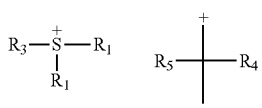

where $R_1$ to $R_5$ each independently represents C1-16 optionally substituted alkyl group or a substituted or unsubstituted 1 carbocyclic aryl group such as phenyl, naphthyl, etc., or any two or more of $R_1$, $R_2$ and $R_3$ may bond together to form a ring with the sulfur ring (e.g. a 5, 6 or 7 membered ring with the sulfur atom). A preferred example of the carbocyclic aryl group includes a $C_{6-14}$ monocyclic or a condensed ring aryl group. Preferred examples of the substituent on the aryl group include an alkyl group, a haloalkyl group, a cycloalkyl group, an aryl group, an alkoxy group, a nitro group, a carboxyl group, an alkoxycarbonyl group, a hydroxyl group, mercapto group, and a halogen atom.

Specifically preferred PAGs of the invention include the following:

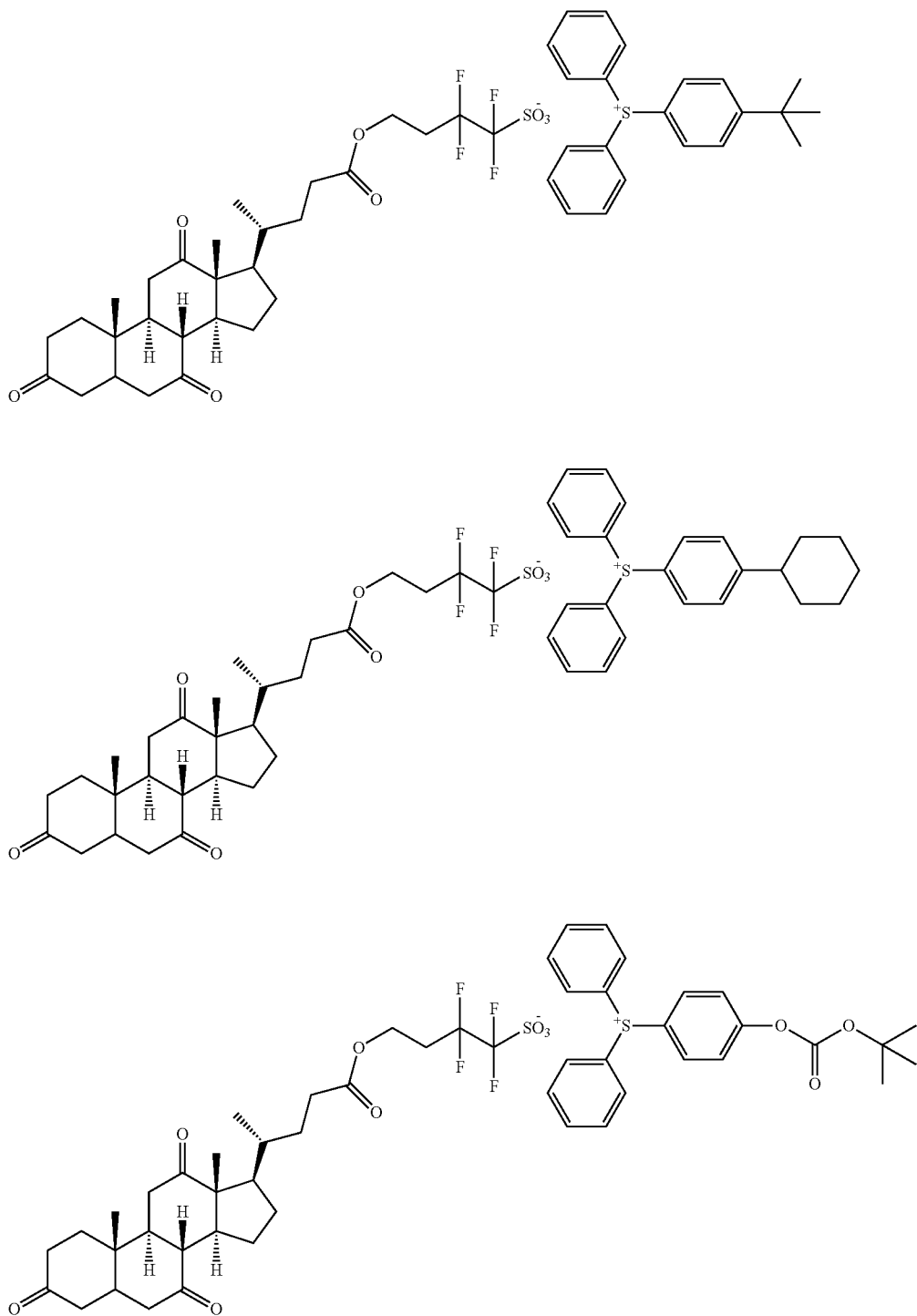

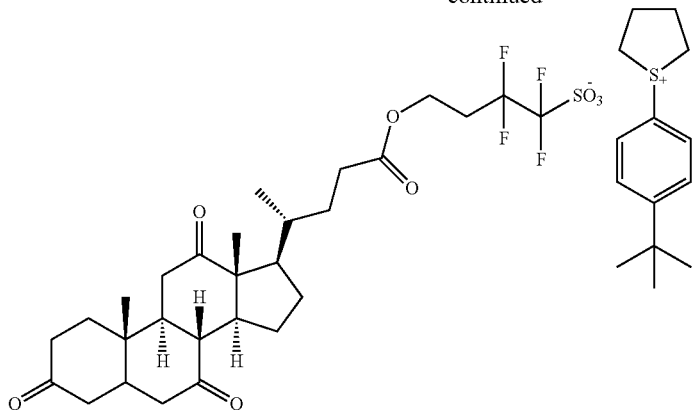

The following Scheme 1 exemplifies suitable approach for synthesis of PAGs of the invention:

Synthetic scheme for DHC-TFBS PAG

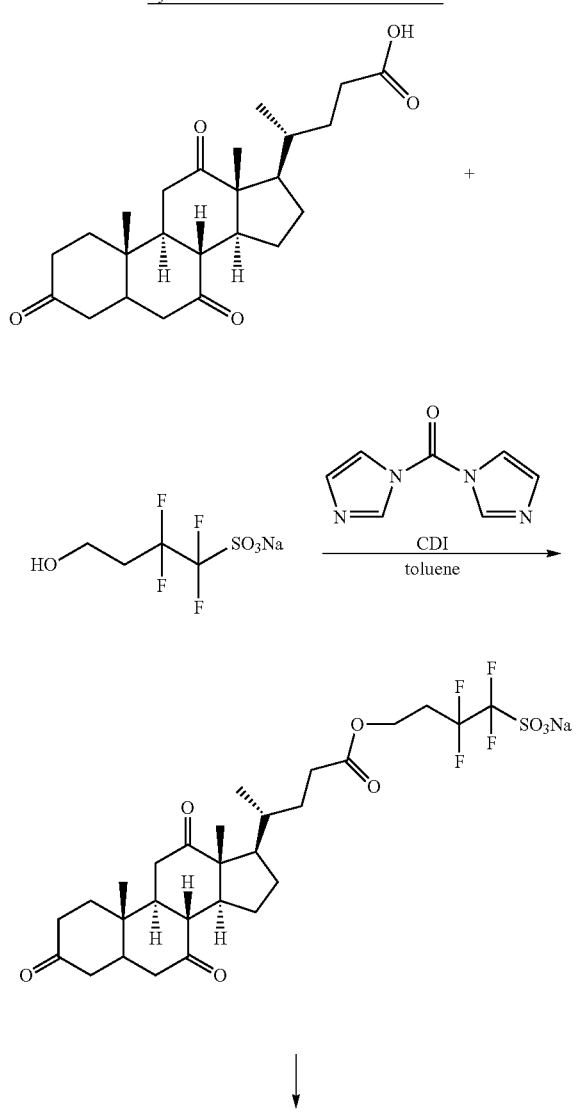

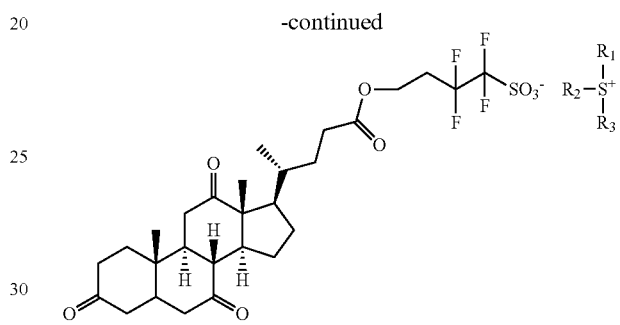

As stated herein above, various substituent groups of PAGs of the invention may be optionally substituted. Substituted moieties are suitably substituted at one or more available positions by, e.g., halogen such as F, Cl Br and/or I, nitro, cyano, sulfono, alkyl including $C_{1-16}$ alkyl with $C_{1-8}$ alkyl being preferred, haloalkyl such as fluoroalkyl (e.g. trifluoromethyl) and perhaloalkyl such as perfluoro-$C_{1-4}$alkyl, alkoxy including $C_{1-16}$ alkoxy having one or more oxygen linkages with $C_{1-8}$ alkoxy being preferred, alkenyl including $C_{2-12}$ alkenyl with $C_{2-8}$ alkenyl being preferred, alkenyl including $C_{2-12}$ alkynyl with $C_{2-8}$ alkynyl being preferred, aryl such as phenyl or naphthyl and substituted aryl such as halo, alkoxy, alkenyl, alkynyl and/or alkyl substituted aryl, preferably having the number of carbon atoms mentioned above for corresponding groups. Preferred substituted aryl groups include substituted phenyl, anthracenyl and naphthyl.

As used herein, the term alkyl, alkenyl and alkynyl unless otherwise modified refers to both cyclic and noncyclic groups, although of course cyclic groups will comprise at least three carbon ring members. Alkenyl and alkynyl groups of compounds of the invention have one or more unsaturated linkages, typically 1 to about 3 or 4 unsaturated linkages. Also, the terms alkenyl and alkynyl as used herein refer to both cyclic and noncyclic groups, although straight or branched noncyclic groups are generally more preferred.

Alkoxy groups of PAG compounds of the invention have one or more oxygen linkages, typically 1 to about 5 or 6 oxygen linkages. Alkylthio groups of PAGs of the invention have one or more thioether linkages, typically 1 to about 5 or 6 thioether linkages. Alkylsulfinyl groups of PAG compounds of the invention have one or more sulfinyl (SO) linkages, typically 1 to about 5 or 6 sulfinyl linkages. Alkylsulfonyl groups of PAG compounds of the invention have one or more sulfonyl (SO$_2$) linkages, typically 1 to about 5 or 6 sulfonyl linkages. Preferred alkylamino groups of PAG compounds of the invention include those groups having one or more primary, secondary and/or tertiary amine groups, preferably 1 to about 3 or 4 amine groups. Suitable alkanoyl groups have one or more carbonyl groups, typically 1 to about 4 or 5 carbonyl groups. Alkoxy, alkylthio, alkylsulfinyl, alkylsulfonyl, alkanoyl and other groups may be suitably either linear or branched. Carbocyclic aryl as used herein refers to non-hetero aromatic groups that have 1 to 3 separate or fused rings and 6 to about 18 carbon ring members and may include e.g. phenyl, naphthyl, biphenyl, acenaphthyl, phenanthracyl, and the like. Phenyl and naphthyl are often preferred. Suitable heteroaromatic or heteroaryl groups will have 1 to 3 rings, 3 to 8 ring members in each ring and from 1 to about 3 hetero atoms (N, O or S). Specifically suitable heteroaromatic or heteroaryl groups include e.g. courmarinyl, quinolinyl, pyridyl, pyrazinyl, pyrimdinyl, furyl, pyrrolyl, thienyl, thiazolyl, oxazolyl, imidazolyl, indolyl, benzofuranyl, and benzothiazole.

As discussed above, PAGs of the invention are useful as the radiation sensitive component in photoresist compositions, including both positive-acting and negative-acting chemically amplified resist compositions.

The photoresists of the invention typically comprise a resin binder and a photoactive component of the invention as described above. Preferably the resin binder has functional groups that impart alkaline aqueous developability to the resist composition. For example, preferred are resin binders that comprise polar functional groups such as hydroxyl or carboxylate. Preferably the resin binder is used in a resist composition in an amount sufficient to render the resist developable with an aqueous alkaline solution.

Preferably, a photoacid generator compound of the invention is employed in a chemically amplified positive-acting resist. A number of such resist compositions have been described, e.g., in U.S. Pat. Nos. 4,968,581; 4,883,740; 4,810,613 and 4,491,628 and Canadian Patent Application 2,001,384, all of which are incorporated herein by reference for their teaching of making and using chemically amplified positive-acting resists. In accordance with the present invention, those prior resist compositions are modified by substitution of the photoactive component of the invention as the radiation sensitive component.

PAGs of the invention also are preferably used with polymers that contain one or more photoacid-labile groups and that are substantially, essentially or completely free of phenyl or other aromatic groups. Such photoresist compositions are particularly useful for imaging with sub-200 nm radiation such as 193 nm radiation.

For example, preferred polymers contain less than about 5 mole percent aromatic groups, more preferably less than about 1 or 2 mole percent aromatic groups, more preferably less than about 0.1, 0.02, 0.04 and 0.08 mole percent aromatic groups and still more preferably less than about 0.01 mole percent aromatic groups. Particularly preferred polymers are completely free of aromatic groups. Aromatic groups can be highly absorbing of sub-200 nm radiation and thus are undesirable for polymers used in photoresists imaged with such short wavelength radiation.

Suitable polymers that are substantially or completely free of aromatic groups and may be formulated with a PAG of the invention to provide a photoresist for sub-200 nm imaging are disclosed in European application EP930542A1 of the Shipley Company.

Suitable polymers that are substantially or completely free of aromatic groups suitably contain acrylate units such as photoacid-labile acrylate units as may be provided by polymerization of methyladamanatylacrylate, methyladamanylmethacrylate, ethylfencylacrylate, ethylfencylmethacrylate, and the like; fused non-aromatic alicyclic groups such as may be provided by polymerization of a norbornene compound or other alicyclic compound having an endocyclic carbon-carbon double bond; an anhydride such as may be provided by polymerization of maleic anhydride; and the like.

Preferred negative-acting compositions of the invention comprise a mixture of materials that will cure, crosslink or harden upon exposure to acid, and a photoactive component of the invention.

Particularly preferred negative acting compositions comprise a resin binder such as a phenolic resin, a crosslinker component and a photoactive component of the invention. Such compositions and the use thereof has been disclosed in European Patent Applications 0164248 and 0232972 and in U.S. Pat. No. 5,128,232 to Thackeray et al. Preferred phenolic resins for use as the resin binder component include novolaks and poly(vinylphenol)s such as those discussed above. Preferred crosslinkers include amine-based materials, including melamine, glycolurils, benzoguanamine-based materials and urea-based materials. Melamine-formaldehyde resins are generally most preferred. Such crosslinkers are commercially available, e.g. the melamine resins sold by American Cyanamid under the trade names Cymel 300, 301 and 303. Glycoluril resins are sold by American Cyanamid under trade names Cymel 1170, 1171, 1172, urea-based resins are sold under the trade names of Beetle 60, 65 and 80, and benzoguanamine resins are sold under the trade names Cymel 1123 and 1125.

Photoresists of the invention also may contain other materials. For example, other optional additives include actinic and contrast dyes, anti-striation agents, plasticizers, speed enhancers, sensitizers, etc. Such optional additives typically will be present in minor concentration in a photoresist composition except for fillers and dyes which may be present in relatively large concentrations such as, e.g., in amounts of from 5 to 30 percent by weight of the total weight of a resist's dry components.

A preferred optional additive of resists of the invention is an added base, particularly tetrabutylammonium hydroxide (TBAH), which can enhance resolution of a developed resist relief image. The added base is suitably used in relatively small amounts, e.g. about 1 to 10 percent by weight relative to the PAG, more typically 1 to about 5 weight percent. Other preferred basic additives include ammonium sulfonate salts such as piperidinium p-toluenesulfonate and dicyclohexylammonium p-toluenesulfonate; alkyl amines such as tripropylamine and dodecylamine; aryl amines such as diphenylamine, triphenylamine, aminophenol, 2-(4-aminophenyl)-2-(4-hydroxyphenyl)propane, etc.

The resin binder component of resists of the invention are typically used in an amount sufficient to render an exposed coating layer of the resist developable such as with an aqueous alkaline solution. More particularly, a resin binder will suitably comprise 50 to about 90 weight percent of total solids of the resist. The photoactive component should be present in an amount sufficient to enable generation of a latent image in a coating layer of the resist. More specifically, the photoactive component will suitably be present in an amount of from about 1 to 40 weight percent of total solids of a resist. Typically, lesser amounts of the photoactive component will be suitable for chemically amplified resists.

The photoresists of the invention are generally prepared following known procedures with the exception that a PAG of the invention is substituted for prior photoactive compounds used in the formulation of such photoresists. For example, a resist of the invention can be prepared as a coating composition by dissolving the components of the photoresist in a suitable solvent such as, e.g., a glycol ether such as 2-methoxyethyl ether (diglyme), ethylene glycol monomethyl ether, propylene glycol monomethyl ether; lactates such as ethyl lactate or methyl lactate, with ethyl lactate being preferred; propionates, particularly methyl propionate and ethyl propionate; a Cellosolve ester such as methyl Cellosolve acetate; an aromatic hydrocarbon such as toluene or xylene; or a ketone such as methylethyl ketone, cyclohexanone and 2-heptanone. Typically the solids content of the photoresist varies between 5 and 35 percent by weight of the total weight of the photoresist composition.

The photoresists of the invention can be used in accordance with known procedures. Though the photoresists of the invention may be applied as a dry film, they are preferably applied on a substrate as a liquid coating composition, dried by heating to remove solvent preferably until the coating layer is tack free, exposed through a photomask to activating radiation, optionally post-exposure baked to create or enhance solubility differences between exposed and nonexposed regions of the resist coating layer, and then developed preferably with an aqueous alkaline developer to form a relief image. The substrate on which a resist of the invention is applied and processed suitably can be any substrate used in processes involving photoresists such as a microelectronic wafer. For example, the substrate can be a silicon, silicon dioxide or aluminum-aluminum oxide microelectronic wafer. Gallium arsenide, ceramic, quartz or copper substrates may also be employed. Substrates used for liquid crystal display and other flat panel display applications are also suitably employed, e.g. glass substrates, indium tin oxide coated substrates and the like. A liquid coating resist composition may be applied by any standard means such as spinning, dipping or roller coating. The exposure energy should be sufficient to effectively activate the photoactive component of the radiation sensitive system to produce a patterned image in the resist coating layer. Suitable exposure energies typically range from about 1 to 300 mJ/cm². As discussed above, preferred exposure wavelengths include sub-200 nm such as 193 nm. Suitable post-exposure bake temperatures are from about 50° C. or greater, more specifically from about 50 to 140° C. For an acid-hardening negative-acting resist, a post-development bake may be employed if desired at temperatures of from about 100 to 150° C. for several minutes or longer to further cure the relief image formed upon development. After development and any post-development cure, the substrate surface bared by development may then be selectively processed, for example chemically etching or plating substrate areas bared of photoresist in accordance with procedures known in the art. Suitable etchants include a hydrofluoric acid etching solution and a plasma gas etch such as an oxygen plasma etch.

The following non-limiting example is illustrative of the invention.

EXAMPLE 1

Synthesis of TPS DHC TFBS

The three steps synthesis of TBPTMS 3OH-Ad TFBS is described in the Scheme B. The details synthetic procedures for each step are outlined below.

Scheme B

Step 1:

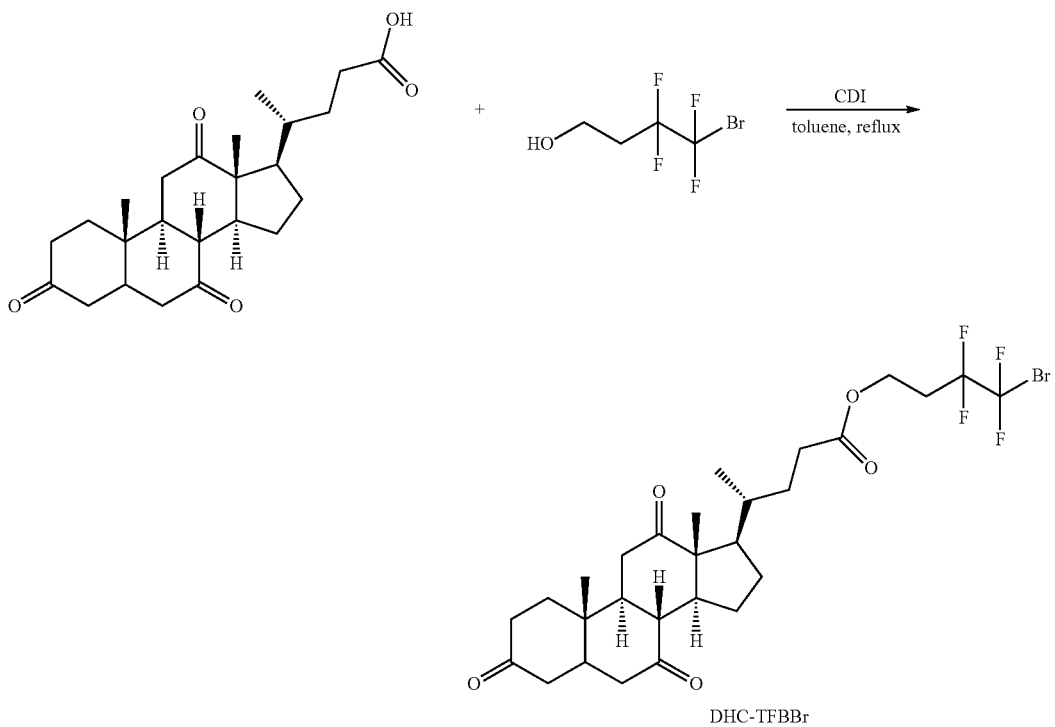

DHC-TFBBr

Step 2:
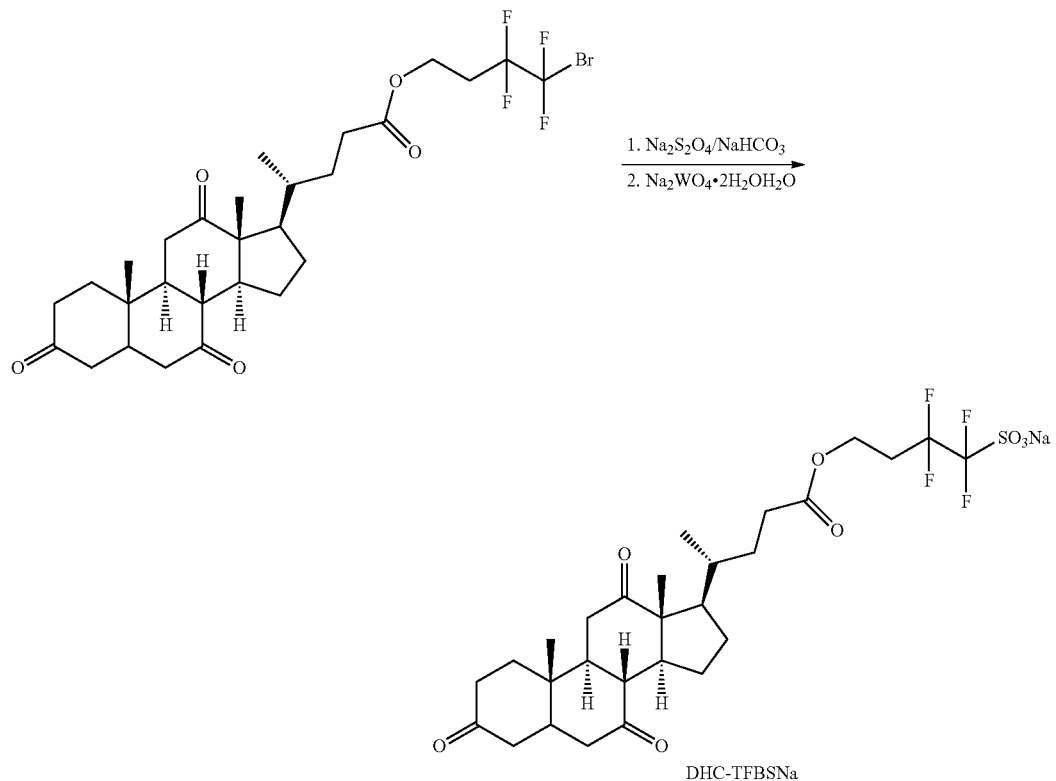
Step 3:
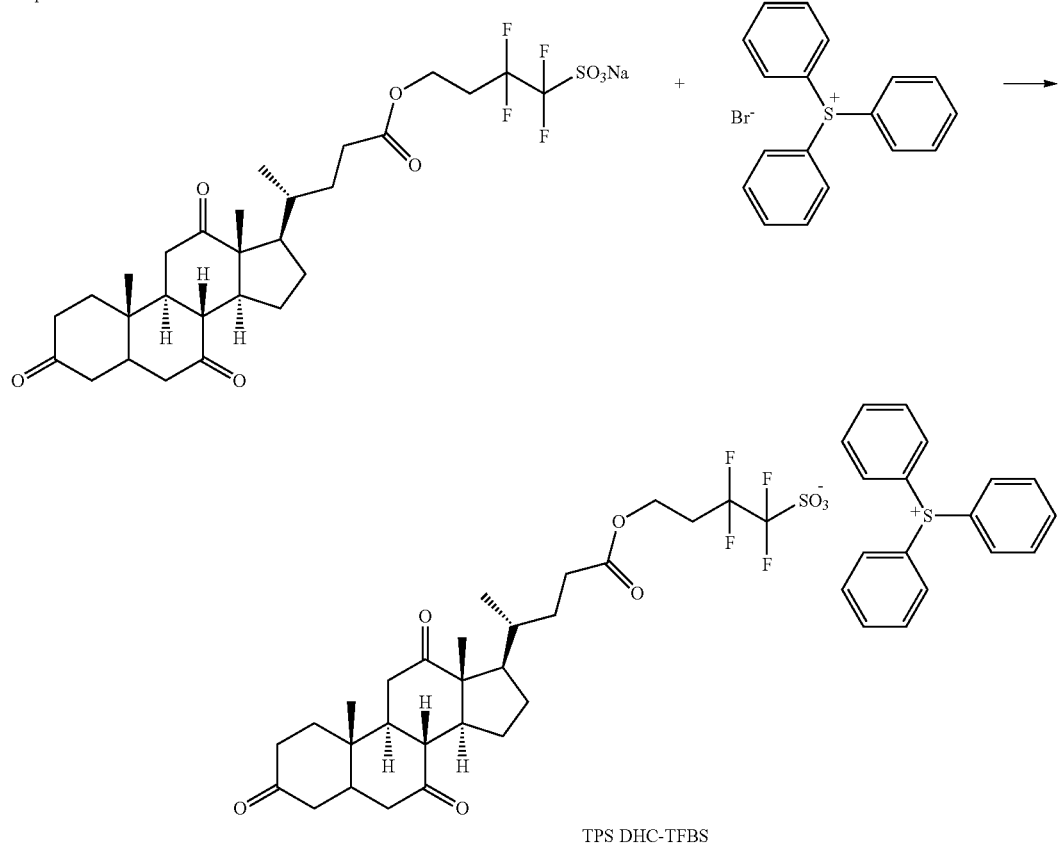

Step 1: Synthesis of DHC-TFBBr:

To a 3 L flask were added 120 g of Dehydrocholic acid (298.12 mmol), 50.7 g of 1,1'-carbonyldiimidazole (CDI) and 1800 mL toluene under a nitrogen sweep. The mixture was held at room temp for 2-3 hrs. The mixture was heated to reflux, then 70.40 g of 4-bromo-3,3,4,4-tetrafluoro-butan-1-ol (312.9 mmol) was added over a 5 min period. The mixture slowly becomes an amber colored solution with overnight heating. The reaction was cooled to 25 C, added to a separatory funnel then washed with water (10×800 ml) until the pH was equal to the pH of the DI water. To the top (amber colored) toluene layer was added $MgSO_4$ and 15 g of activated charcoal. This mixture was stirred for 2 hrs and then filtered. The filtrate (toluene) was removed under reduced pressure resulting in a white solid. This solid was vacuum dried at 70 C for 18 hrs leaving 136 g of product (75% yield). The product DHC-TFBBr was used in step 2.

Step 2: Synthesis of DHC-TFBSNa:

The product DHC-TFBBr (136 g) from step 1 was combined in a 3 L flask with 78 g sodium thiosufite, 56.8 g sodium bicarbonate, 1300 ml of acetonitrile and 650 ml of deionized water. This mixture was held at 60 C for 16 hrs. The mixture was cooled to room temp. The acetonitrile layer was collected and placed in a 2 L flask and the water was azeotroped off by removing ~50% of the acetonitrile. Any salts which precipitated out were removed and the filtrate was poured into 10 L of methyl t-butyl ether. The solid was collected by filtration and dried. 138.5 g of sulfinate salt was obtained which were added to a mixture of 750 ml of acetonitrile and 350 ml of DI water. To the mixture was added 150 mg of $NaWO_4.2H_2O$ and 38.2 g of 30% hydrogen peroxide. The solution was stirred for 2-3 hrs at room temp. The product DHC-TFBSNa was obtained after usual workup as colorless solid. Yield 100 g (71%). The product was used in the 3rd step.

Step 3: Synthesis of TPS DHC-TFBS:

A mixture made of 111 g of DHC-TFBSNa, 60.50 g of triphenyl sulfonium bromide in 750 ml methylene chloride and 100 ml of deionized water was stirred at room temperature for 18 hours. The layers were separated and the bottom organic layer was washed with 10×500 ml of deionized water. The methylene chloride was dried over $MgSO_4$ then reduced in volume by 40%. The methylene chloride solution was slowly added to 10 L of Methyl t-butyl ether. The solid was collected and dried leaving 139 g of TPS DHC-TFBS. The product was refluxed overnight in 500 ml of MTBE, collected and dried leaving 131 g of analytically pure product.

EXAMPLE 3

Photoresist Preparation and Lithographic Processing

A photoresist of the invention is prepared by mixing the following components with amounts expressed as weight percent based on total weight of the resist compositions:

| Resist components | Amount (wt. %) |
|---|---|
| Resin binder | 15 |
| Photoacid generator | 4 |
| Ethyl lactate | 81 |

The resin binder is a terpolymer (2-methyl-2-adamantyl methacrylate/beta-hydroxy-gamma-butyrolactone methacrylate/cyano-norbornyl methacrylate. The photoacid generator is the compound TPS DHC-TFBS, as prepared in Example 1 above. Those resin and PAG components are admixed in the ethyl lactate solvent.

The formulated resist composition is spin coated onto HMDS vapor primed 4 inch silicon wafers and softbaked via a vacuum hotplate at 90° C. for 60 seconds. The resist coating layer is exposed through a photomask at 193 nm, and then the exposed coating layers are post-exposure baked at 110° C. The coated wafers are then treated with 0.26N aqueous tetrabutylammonium hydroxide solution to develop the imaged resist layer.

What is claimed is:

1. A photoacid generator compound represented by a structure:

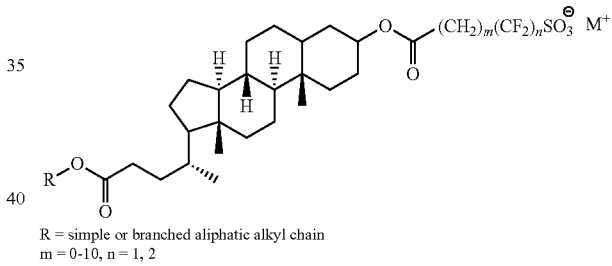

R = simple or branched aliphatic alkyl chain
m = 0-10, n = 1, 2 wherein $M^+$ represents a cation group, and the definition of the group R, m and n are defined directly below the structure.

2. A photoacid generator compound selected from:

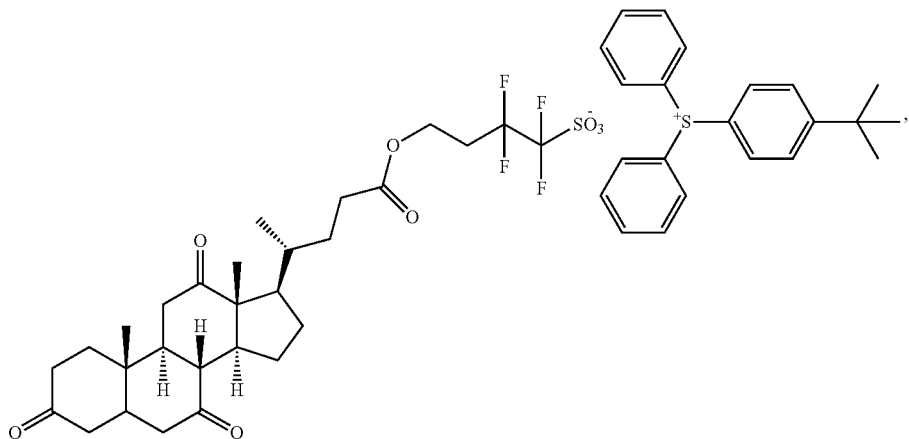

-continued

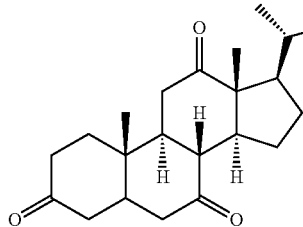
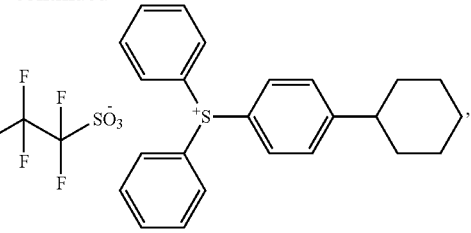

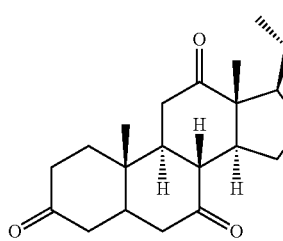
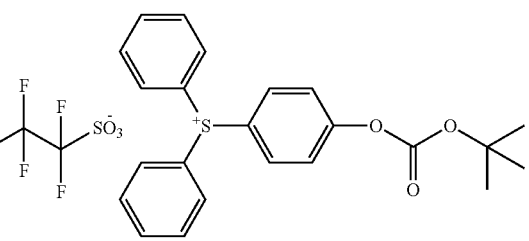
and

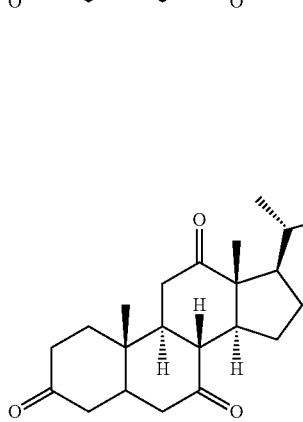
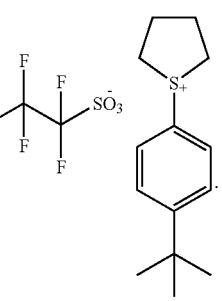

3. A photoresist composition comprising a resin component and a photoacid generator compound of claim 1.

4. A photoresist composition comprising a resin component and a photoacid generator compound of claim 2.

5. A method for forming a photoresist relief image comprising:
(a) applying a coating layer of a photoresist composition of claim 3 on a substrate;
(b) exposing the photoresist coating layer to patterned activating radiation and developing the exposed photoresist layer to provide a relief image.

6. A method for forming a photoresist relief image comprising:
(a) applying a coating layer of a photoresist composition of claim 4 on a substrate;
(b) exposing the photoresist coating layer to patterned activating radiation and developing the exposed photoresist layer to provide a relief image.

* * * * *